United States Patent [19]

Martin

[11] Patent Number: 5,073,913

[45] Date of Patent: Dec. 17, 1991

[54] APPARATUS FOR ACCELERATION AND APPLICATION OF NEGATIVE IONS AND ELECTRONS

[75] Inventor: Ronald L. Martin, LaGrange, Ill.

[73] Assignee: ACCTEK Associates, Inc., LaGrange, Ill.

[21] Appl. No.: 606,536

[22] Filed: Oct. 31, 1990

Related U.S. Application Data

[62] Division of Ser. No. 186,183, Apr. 26, 1988, Pat. No. 4,992,746.

[51] Int. Cl.$^5$ ............................................. H05H 13/04
[52] U.S. Cl. ...................................... 378/34; 378/119; 378/65; 328/233; 328/235
[58] Field of Search ...................... 378/34, 119, 64, 65; 250/489, 492.1, 492.2, 492.3; 328/233, 235

[56] References Cited

U.S. PATENT DOCUMENTS

| | | | |
|---|---|---|---|
| 3,328,708 | 6/1967 | Smith et al. | 328/235 |
| 3,344,435 | 9/1967 | Blewett | 328/235 |
| 3,986,026 | 10/1976 | Martin | 250/358.1 |
| 4,780,683 | 10/1988 | Nakata | 328/228 |
| 4,992,746 | 2/1991 | Martin | 378/34 |

*Primary Examiner*—Carolyn E. Fields
*Assistant Examiner*—David P. Porta
*Attorney, Agent, or Firm*—McAndrews, Held & Malloy, Ltd.

[57] ABSTRACT

An apparatus for generating X-rays from electron synchrotron radiation or beams of accelerated ions for ion radiography or ion therapy includes a source of electrons and a source of ions, both of which are connectable to preaccelerators. The preaccelerators supply the appropriate type of charged particle to a synchrotron accelerator which accelerates ions to an energy level that is appropriate for radiography or therapy and which accelerates electrons to a level that generates X-rays by synchrotron radiation in a useful frequency range. The accelerator system also includes a storage ring into which particles are switched and circulated for later use. Electrons are extracted from the synchrotron and injected into the storage ring by fast extraction using a kicker magnet and a septum magnet. They then circulate in the storage ring for periods of hours generating X-rays which may be used for lithography of computer chips with submicron resolution. The energy loss because of this radiation is continuously replaced by a radio-frequency acceleration system. During the period that electrons are circulating in the storage ring, the synchrotron may be utilized to accelerate ions for ion radiography or ion therapy with beam extracted from the synchrotron by stripping extraction through thin foils. Other simultaneous uses for the ions or electrons from the preaccelerator may prove advantageous.

11 Claims, 6 Drawing Sheets

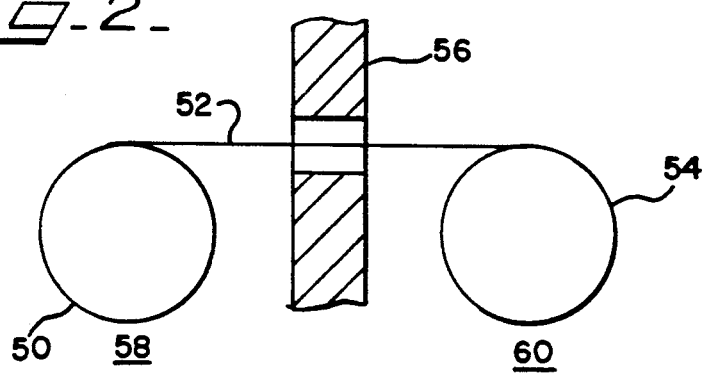
_Fig. 2._
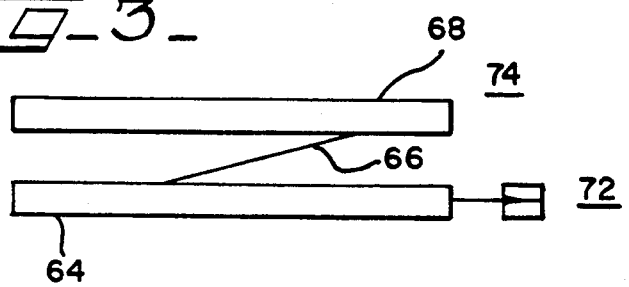
_Fig. 3._
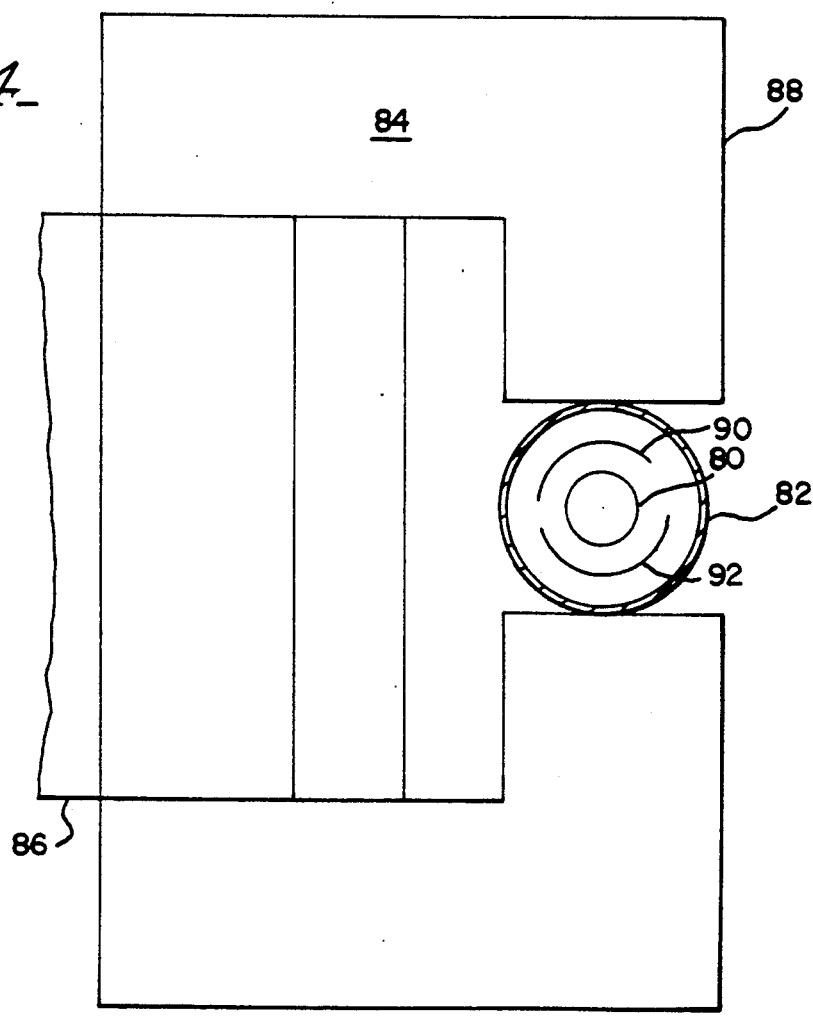
_Fig. 4._

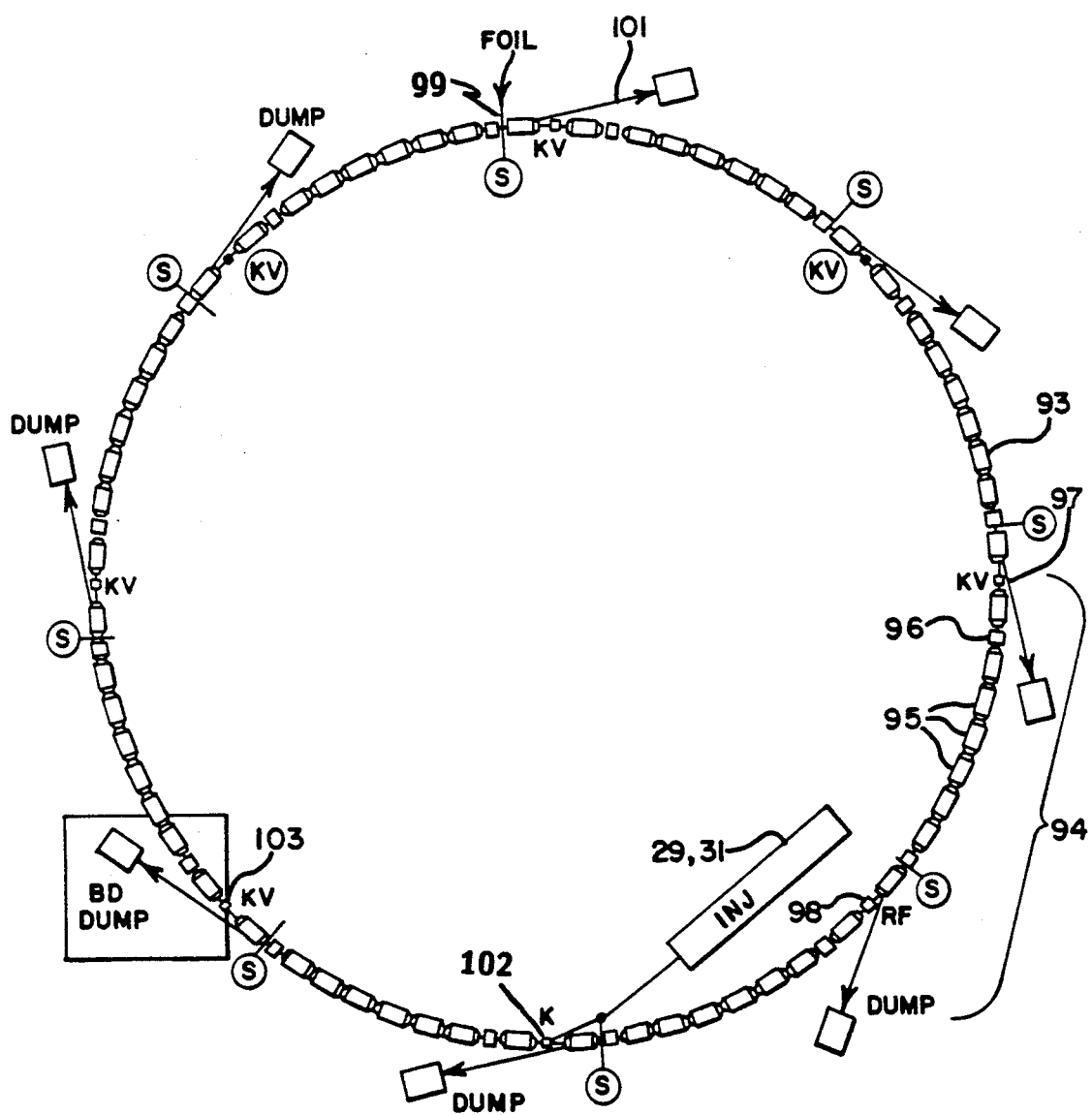
FIG_5_

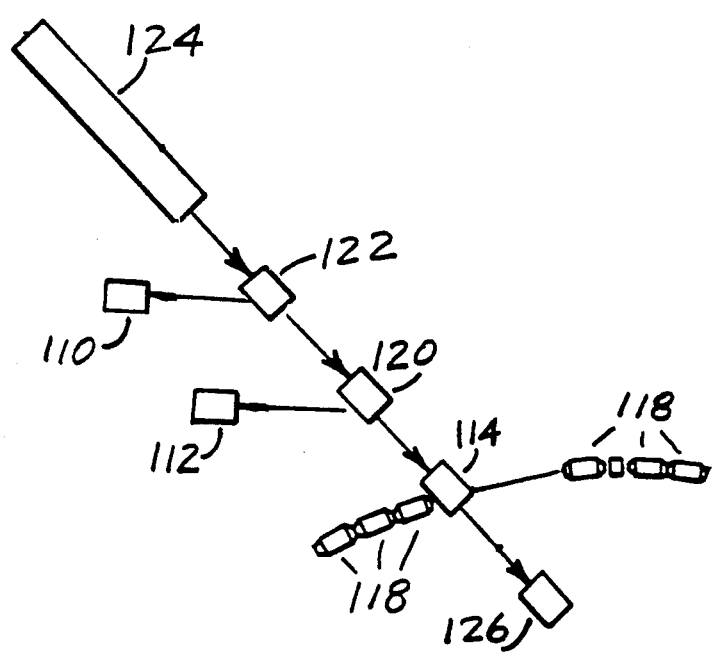
FIG_6

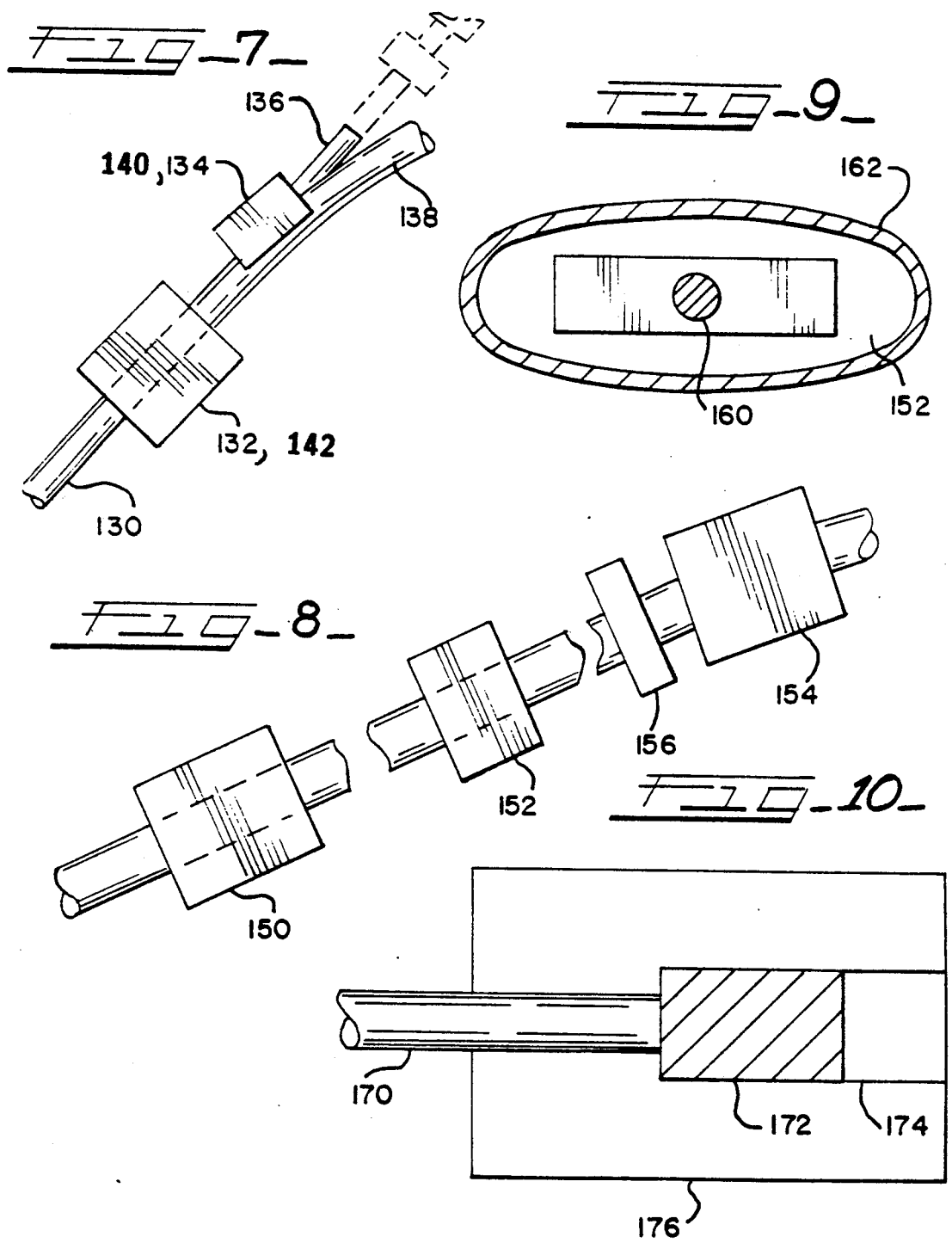

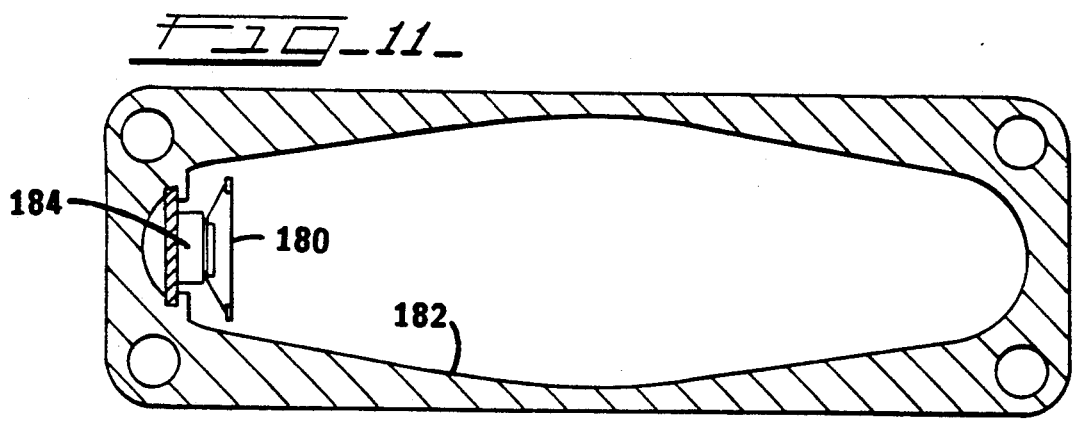
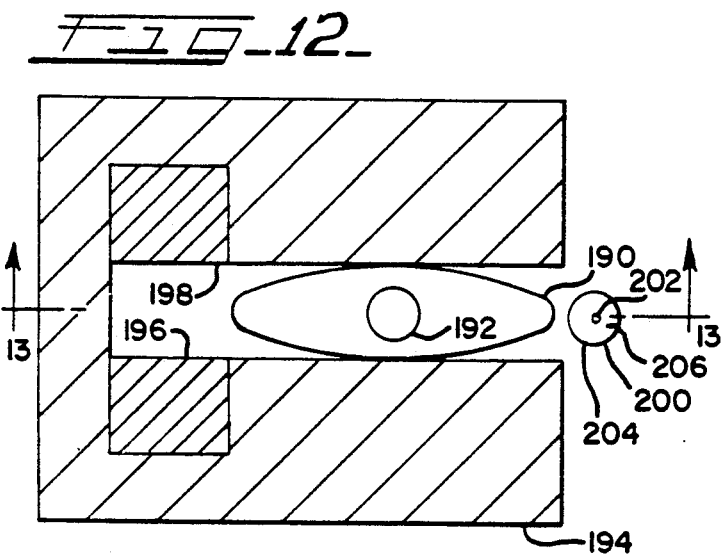
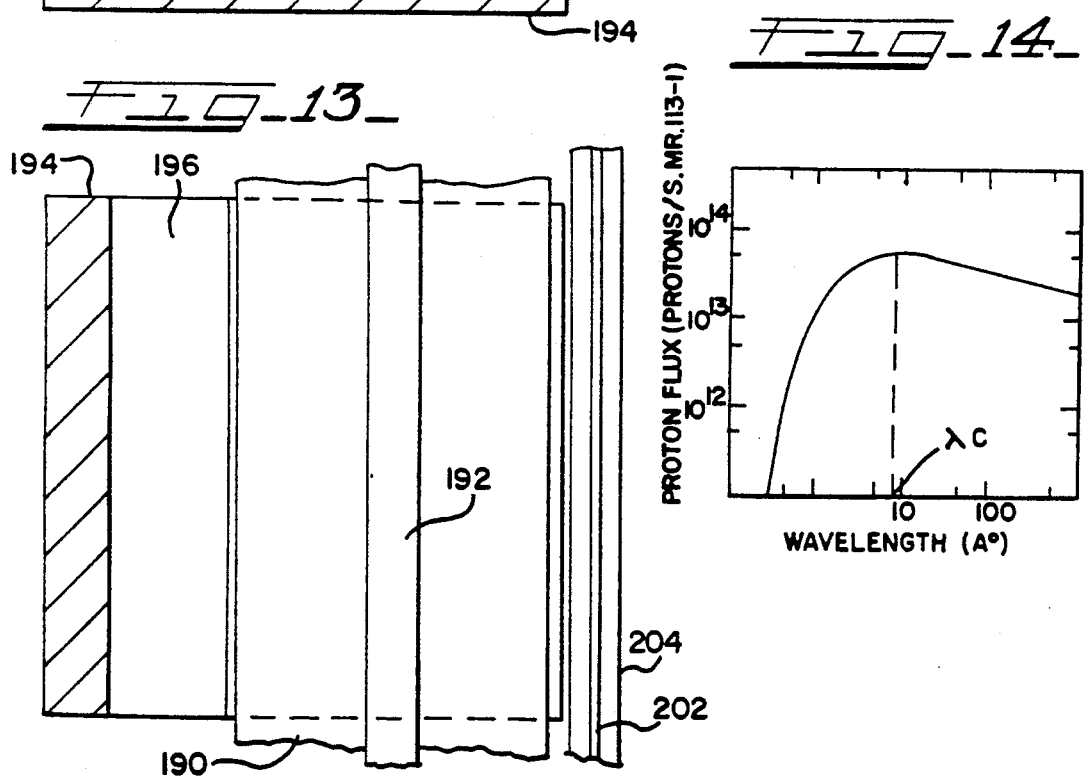

APPARATUS FOR ACCELERATION AND APPLICATION OF NEGATIVE IONS AND ELECTRONS

This invention was made with Government support under grant Numbers IR43 CA41218-01 and IR43 CA23407-01 awarded by the National Institute of Health. The Government has certain rights in the invention.

This is a division of Application Ser. No. 186,183, filed Apr. 26, 1988 now U.S. Pat. No. 4992746.

This invention relates to particle accelerators that are usable for multiple purposes, to the simultaneous use of getter strips for two important functions in electron storage rings, to much enhanced flexibility of magnet arrangements in synchrotrons and storage rings, and to several unique and novel accelerator concepts that relate to the use of negative ions. The latter include stretcher rings, accumulator rings for ions, accelerator rings of unusually low residual activity, novel methods of accelerator alignment and tuneup, and a novel method of precision local vacuum measurement in rings under high vacuum. A stretcher ring is well known to be a storage ring in which a circulating pulse of particles that is bunched in space is caused to be stretched in time by repeated extraction of small portions of the circulating pulse. An accumulator ring is well known to be a storage ring in which a number of pulses has been loaded into the ring to produce a number of circulating particles that can be extracted to produce a pulse having more particles than the individual loading pulses.

The use of accelerators for multiple purposes relates, in particular, to a particle accelerator system that can be used to store electrons to produce X-rays by synchrotron radiation, and also accelerate protons or other ions to be used for tissue therapy or radiography. An important use of the X-rays that are produced by the circulating electron beam will be in the lithography of integrated circuits.

The methods presently used for making integrated circuits involve the preparation of masks that are used with visible or ultraviolet light to create patterns on semiconductor materials. These patterns are etched or otherwise treated to produce desired patterns on the semiconductor material. Line spacings of the order of one micron are being produced by this method. However, such spacings are approaching the limit of resolution of visible and ultraviolet light. This resolution can be increased by the use of X-rays because of their shorter wave length. Conventional methods of generating X-rays such as the Coolidge tube produce X-rays by the impact of an electron beam on a metal target. Such devices do not produce X-rays of sufficient intensity for use in producing integrated circuits, and they produce X-rays in beams that are not sufficiently precisely defined for the purpose of making semiconductors.

One technique that has been used to expose semiconductors to X-radiation is to generate synchrotron radiation by accelerating electrons in a particle accelerator. A summary of the status of research approaches to the use of synchrotron radiation for this and other purposes is given in a publication entitled "Construction and Commissioning Proceedings of Workshop, October 1985". This is Publication BNL 51959 of the Brookhaven National Laboratory. This publication describes the status of several such facilities, including the National Synchrotron Light Source which is located at Brookhaven National Laboratory. The National Synchrotron Light Source, the Synchrotron Radiation Center at the University of Wisconsin and the Stanford Linear Accelerator Center (SLAC) Synchrotron Radiation Center in Palo Alto represent large-scale laboratories devoted to producing synchrotron radiation for research. Comparable facilities are reported in the publication described above in Japan, Germany, Great Britain, Italy, France, The People's Republic of China, Denmark and Brazil. Two third-generation synchrotron light sources, featuring much higher X-ray intensities that can be achieved by insertion devices, are either under construction or in the final stages of design in the U.S. These are the Advanced Light Source at Lawrence Berkeley Laboratory and the 7-GeV Advanced Photon Source at Argonne National Laboratory. These and each of the facilities described in the Proceedings of the Workshop represents an electron storage ring with an injector that is used only occasionally to fill the ring. Each represents a research installation of major scope, served by numbers of buildings and staffs of substantial size. Such facilities are costly to build and costly to operate. They are permanently emplaced so that users must come to them to obtain the synchrotron radiation for any purpose.

In contrast to the electron storage rings described above, proton synchrotrons and cyclotrons have been and are being used in medical applications. An example of such an accelerator concept for proton radiography is shown in my U.S. Pat. No. 3,986,026, entitled "Apparatus for Proton Radiography," which is incorporated here by reference as if set forth fully. Proton therapy has been carried out for more than ten years at the Harvard Cyclotron Laboratory by physicians from the Massachusetts General Hospital utilizing the Harvard 160 MeV cyclotron. Proton therapy is carried out at facilities designed for physics use in many other parts of the world including Japan, Sweden, and the USSR, while the Lawrence Berkeley Laboratory has utilized helium ions and heavier ions for this purpose. Proton radiography and proton therapy are normally carried out using protons in an energy range of the order of 70–250 MeV (250 MeV per nucleon, or 1000 MeV for helium ions). This energy range is sufficiently low in comparison to the design energy ranges of most present research proton accelerators that most of the experimental work done to date using protons for radiography or therapy has been performed with beams diverted from accelerators that serve large proton physics facilities. It is therefore necessary to bring the patient to the accelerator as it is difficult or impossible to locate the research accelerator at a site that is convenient to a hospital or medical facility. Similarly, the large research electron synchrotrons that are used to produce X-rays by synchrotron radiation cannot be taken to an industrial location, but instead require that the work be brought to them. It is important to design accelerators that are simple, reliable, inexpensive, and able to be utilized near a hospital or industrial location.

Several small electron storage rings have been designed specifically for production of X-rays for lithography of computer chips. These include designs from Cosy Microtech in Berlin, a compact superconducting ring; Oxford Instruments in England, a compact superconducting ring; a room-temperature ring at Brookhaven National Laboratory; a storage ring proposed by Maxwell Laboratories/Brobeck Associates in California; and several such designs in Japan. All use curved magnets, and none are suitable for alternative uses with ions or for dual uses of the injector. Such dual use has not been proposed. All of the units described above use injectors only sporadically to refill the storage ring.

A proton synchrotron of 250 MeV dedicated to proton therapy has been designed by Fermi National Laboratory in Batavia, Illinois, for use at Loma Linda University Medical Center in Loma Linda, California, and is presently under construction. This machine is not suited for negative hydrogen ions (by reason of vacuum and peak magnetic field), has curved magnets, and with electrons would not give adequately short wavelength of synchrotron light to be useful for the lithography application. No dual use of this machine has been proposed.

In many of the electron storage rings that have been built, a problem that has placed a severe limit on the intensity of the beam achieved and the ability to maintain that beam over long periods of time, at least initially, is the trapping of positive ions in the beam. The negative charge of the electron beam represents a potential well for positive ions. These ions are produced by the ionization of the residual gas by the electron beam. They overfocus the electrons and limit the current. The problem is thus sensitive to the achievable vacuum and is exacerbated by desorption of gas from the walls of the vacuum chamber by irradiation with the X-rays produced by the electrons. A long period of time, measured in tens of Ampere-hours of beam divided by the peak achievable beam current, has often been required to reduce the desorption to the point that high currents can be accumulated or maintained. For some installations this has taken as long as a year. This problem has presented such a limit on some operations that designers of systems for producing X-rays through synchrotron radiation have turned to the acceleration of positrons. This eliminates the trapping of positive ions in the beam. However, the use of positrons as particles to be accelerated introduces considerable complexity into the operation of such an accelerator and limits its use to the type of large university facility or national laboratory described above.

The feasibility of using clearing fields to solve the ion-electron problem was demonstrated at the Aladdin facility in Wisconsin. This permitted that facility to overcome a severe current limit of a few milliamperes of stored beam. They also reported the success of single asymmetrical electrodes for this purpose, and the effectiveness of an RF voltage applied between the electrode and the accelerator wall.

The use of non-evaporable getter strips composed of an alloy of zirconium and aluminum was proposed in my U.S. Pat. No. 3,986,026 entitled "Apparatus for Proton Radiography," previously incorporated by reference. Its use was based on very successful experiments in both Europe and the United States, although such strips have not been used in any synchrotron or storage ring to date. The very high distributed pumping speed, 1 liter/sec per square centimeter of pump surface area, can lead to very high vacuum, and the use of such strips has been proposed for the 7 GeV Advanced Photon Source at Argonne and the Large Electron-Positron (LEP) collider in CERN, Switzerland. There has not been any suggestion of the use of such strips for both high-speed vacuum pumping and to provide clearing fields to eliminate the ion-electron problem.

The acceleration of negative hydrogen ions to 250 MeV in a small, weak-field synchrotron and using charge-exchange stripping extraction to utilize the protons for cancer therapy was first proposed by me at a meeting of the Proton Therapy Cooperative Group (PTCOG) at Fermilab in 1985. Slow extraction was required in order to carry c ́ raster scanning of a tumor site and obtain nearly 100% utilization of the extracted beam. This permits keeping the required beam current to 3nA, with the synchrotron operating at 1Hz, including 0.4 sec. each pulse for beam extraction. This current is adequate for treatment of the majority of the cancer sites to which proton therapy is applicable in a period of 2 minutes per fraction. A fraction is that portion of a total radiation dose that is administered in a single sitting. From the point of view of economics, it is very important to keep the circulating current as low as tolerable. However, for the larger tumor sizes, radiotherapists would prefer beams of 20-30 nA. The accelerator designer could significantly increase the injection energy or the magnet aperture to meet this new requirement. Both of these alternatives would significantly increase the cost to the point that the facility would be no longer economically feasible. A more economic alternative is the use of a beam stretcher ring. The synchrotron is cycled at 10Hz, beam is transferred as negative hydrogen ions to the stretcher ring at the peak of the synchrotron cycle, and beam is extracted for therapy from the stretcher ring for 90 of the 100 milliseconds between injection pulses.

The concept of stretcher rings for quite different purposes is not new, although all proposed have included higher field superconducting magnets. A superconducting storage ring in the ZGS tunnel at Argonne National Laboratory was proposed to save electrical power and to increase the duty cycle of experimental use of the proton beam from the existing 25% to nearly 100%. The "Energy Saver/Doubler" at Fermi National Accelerator Laboratory was built to double the energy of the existing ring by having a higher field superconducting ring at 5T in the same tunnel, and to save operating electrical energy by having very long (60-second) pulses at full field. The latter requires very little energy for the superconductors, and cycles the synchrotron much less frequently than previously. This is quite the opposite purpose proposed here. The facility is presently called the TEVATRON.

At one of the later meetings of PTCOG, a desire was expressed to carry out the fractionated cancer treatment with protons in the time that the therapist could ask a patient to hold his breath (10-15 seconds), rather than the two minutes previously discussed. The rationale for this request was that to make use of the higher precision of dose localization available with protons, patient motion could not longer be tolerated. To accomplish this order of magnitude increase in instantaneous rate with a synchrotron has seemed out of question in terms of economic feasibility. However, a combination of two accepted techniques appear to solve even this problem. These are the acceleration of negative hydrogen or deuterium ions in a rapid-cycling synchrotron, fast extraction from the synchrotron, and charge-exchange (stripping) injection into the accumulator ring. By this technique, a large number of synchrotron pulses (200-400) can be injected into the accumulator ring until enough protons for the complete irradiation are accumulated. These protons can then be extracted in less than 10 seconds in any of the standard ways. The high injection energy (up to 250 Mev) insures that the space-charge limit of the accumulator ring will be high enough to contain an adequate number of protons.

Charge-exchange injection by stripping H. ions in a thin foil to reach high intensity in a small ring is presently a very commonly used technique. It was first carried out in an operational way on the ZGS at Argonne National Laboratory, the Rapid Cycling Synchrotron of the Argonne Intense Pulsed Neutron Source, the Booster Synchrotron at Fermilab, the Alternating Gradient Synchrotron (AGS) at Brookhaven, the KEK (Japan) Booster Synchrotron, the Los Alamos Proton Storage Ring, and the Rutherford (England) Intense Neutron Source. All of these facilities are physics facilities having expensive injectors, not economically suited for the present application. In all of these facilities, the $H^-$ion beam is produced from a linear accelerator (linac); no transfer from one synchrotron to another has been proposed before.

Most dipole magnets used in synchrotrons and storage rings are curved magnets. The only exception to this practice seems to be those rings whose circumference is so large that the sagitta of long straight magnets is small enough that it does not present a problem. The sagitta is defined as the distance along a radius of a circle from the perpendicular intersection of the radius with a chord to the circumference of the circle. Examples are the rings at Fermilab (1000 magnets in a circumference of about 3 miles) and equivalent rings in Switzerland and the USSR. Two of the advantages of short, straight magnets, that of simplicity of construction and cost were recognized in my U.S. Pat. No. 3,986,026, cited above. A very significant advantage of that choice, however, that of the flexibility of arrangement of the dipoles and quadruples for many different applications, including lithography, was not obvious or recognized at the time. This flexibility has recently allowed me to propose a facility for synchrotron radiation in which the same dipole magnets were arranged into a full energy storage ring, and a smaller number into a smaller and lower energy injector synchrotron.

Negative ions are presently in common use for rather specific applications. Sources of negative ions are required as inputs to tandem accelerators, with polarity changing from negative to positive in the high-voltage terminal to achieve additional acceleration from that terminal back to ground potential. Negative hydrogen ions are accelerated in the sector focussed cyclotron, TRIUMPF, in Vancouver, British Columbia, where they are passed through a movable foil at high energy to provide protons of variable energy outside the accelerator. No means of direct extraction of the negative hydrogen ions is provided. Intense negative ion sources at energies of 100-200 keV, with neutralization to produce neutral beams for injection into Tokamaks are in use or under development. The widespread use of $H^-$ions for change exchange injection into synchrotrons or storage rings as a superior injection process has been discussed above. My U.S. Pat. No. 3,986,026 suggested acceleration of negative hydrogen ions to the 100-200 MeV energy range with change-exchange extraction to utilize protons in the radiographic work station. There has not to date been any suggestion of utilizing high energy (100-200 MeV) negative hydrogen ions, or any other negative ions, directly in work stations. The recent emphasis of Neutral Particle Beams (NPB) with these high energies for the Strategic Defense Initiative, in which negative ions are accelerated and then must be neutralized, has introduced a need for such ions (including $H^-$, $D^-$, and other negative ions) for research. Other applications not presently obvious may also emerge. Production of negative ions of these energies at relatively low intensity (and low cost) requires the concept proposed here: very high vacuum and relatively low magnetic fields to avoid removing the loosely bound electron during the acceleration process, flexible arrangement of bending and focusing magnets to accommodate a variety of possible application requirements, and low residual activity synchrotrons, especially with negative deuterium ions, for easy personnel access.

Also not recognized in the earlier concepts were the advantages of the short magnets when negative ions are circulated in the ring. These include rings with low residual activity, and the possibility of utilizing stripping extraction in many places for precision alignment and tuneup. The negative ions can also be used for local gas measurements.

SUMMARY OF THE INVENTION

It is an object of the present invention to provide the multiple use of ions and electrons in an accelerator facility including preaccelerators, synchrotron and storage ring. This is particularly advantageous when the storage ring is utilized for long time circulation of electrons, and the other valuable components of the facility, the preaccelerators and the synchrotron, are needed only sporadically to fill the storage ring with electrons.

It is a further object of the present invention to provide a simultaneous use of non-evaporable getter strips in electron storage rings for two very important functions: as a distributed high-speed pump to achieve high vacuum, and as clearing fields to prevent positive ions from being trapped in the potential well of the electron beam, thereby overfocusing and destroying the latter.

It is a further object of the present invention to utilize the storage ring as a duty-cycle stretcher ring with stripping extraction of negative ions to give nearly 100% duty cycle while at the same time achieving an intensity an order of magnitude higher by cycling the synchrotron at a rapid rate. This could be particularly useful for medical applications of these ions.

It is another object of the present invention to utilize the storage ring as a full-energy accumulator ring to accumulate a large number of synchrotron pulses and extract this accumulated high-intensity beam in a short period of time. This is particularly useful for medical applications in which it is desired to complete a radiation treatment for cancer in the time that a person might be requested to hold his breath, of the order of 10-15 seconds. For this purpose, it is necessary to accelerate negative ions in the synchrotron with fast extraction and stripping injection into the storage ring, and to use normal extraction of positive ions from the storage ring.

It is a further object of the present invention to provide the unusual use in small synchrotrons and storage rings of small straight dipole magnets. This choice has a number of surprising consequences. Besides being simpler to construct, less costly, and leading to an important increase in the flexibility of application of the rings, the use of small straight dipole magnets with negative ions leads to rings with unusually low residual radioactivity, and provides a unique means of precision alignment and tuneup of rings by multiple extraction points without the need for sophisticated diagnostics within the vacuum chamber of the ring.

It is a further object of the present invention to circulate negative ions in a ring designed for high vacuum with any charged particles and a detector outside the ring to measure the intensity and position of energetic neutral atoms exiting the ring in order to give a measure of the local gas pressure around the ring.

It is another object of the invention to provide high energy negative ions to work stations for direct applications of these ions.

Another object of the invention is to accumulate a beam from a large number of synchrotron pulses so that all of the beam could be utilized in a very short period of time. To accomplish this procedure, it will be necessary to overcome the otherwise unfeasible multiturn injection into the accumulator ring by change exchange injection of negative ions to circulate positive ions in the accumulator ring.

Other objects will become apparent in the course of a detailed description of the invention.

An apparatus for generating X-rays from electron synchrotron radiation and beams of accelerated ions for ion radiography or ion therapy includes a source of electrons and a source of ions, both of which are connectable to a separate preaccelerator. The preaccelerators supply the appropriate type of charged particle to a synchrotron accelerator which accelerates ions to an energy level that is appropriate for radiography or therapy and which accelerates electrons to an energy level suitable for generating X-rays by synchrotron radiation in a useful frequency range. The apparatus also includes a storage ring into which electrons are switched and circulated to supply X-rays continuously from synchrotron radiation. Electrons are extracted from the synchrotron and injected into the storage ring by fast extraction using a kicker magnet and a septum magnet. While electrons are circulating in the storage ring, the ion sources and preaccelerator, electron source and preaccelerator and the synchrotron are no longer needed. They can, therefore, be utilized for other purposes such as accelerating negative ions in the synchrotron to an energy suitable for ion radiography or ion therapy of cancer. The beam is extracted from the synchrotron by passing it through a stripping foil at a specified rate controlled by orbit-warping magnets, and the extracted positive ions are used for the purpose intended. Alternatively, sources and preaccelerators could be utilized for other important applications when not otherwise in use. Another advantageous use of the storage ring is to rapidly cycle the synchrotron to accelerate negative ions to the energy required for the use intended. They are then transferred to the storage ring by the same system used to transfer electrons, and the ions are then slowly extracted from the storage ring by stripping extraction during the time that the synchrotron is recycling to accelerate another pulse of ions. In this way one can obtain the high intensities of a rapid-cycling synchrotron with the nearly 100% duty factor of a storage ring.

BRIEF DESCRIPTION OF THE DRAWINGS

FIG. 2 is a schematic diagram of one arrangement of equipment for the practice of one part of the present invention.

FIG. 3 is a schematic diagram of an alternate arrangement of equipment for the practice of one part of the present invention.

FIG. 4 is a sectional view of a portion of the synchrotron and storage ring.

FIG. 5 is a view of an arrangement of small straight magnets of the synchrotron of the present invention.

FIG. 6 is a block diagram of the injection system for electrons and ions of the present invention.

FIG. 7 is a block diagram of septum extraction from the synchrotron and septum injection into the storage ring.

FIG. 8 is a block diagram of slow charge exchange (stripping) extraction.

FIG. 9 is a sectional view of the vacuum chamber showing the window-frame stripping foil.

FIG. 10 is a sectional view of a beam dump of the present invention.

FIG. 11 is a sectional view of the vacuum chamber showing the location of the non-evaporable getter strip.

FIG. 12 is a sectional end view of a coaxial detector t detect neutral atoms produced by interaction of circulating negative ions with residual gas atoms.

FIG. 13 is a top view of the detector of FIG. 12.

FIG. 14 is a typical X-ray spectrum produced by synchrotron radiation.

DETAILED DESCRIPTION OF THE INVENTION

Figure 1:
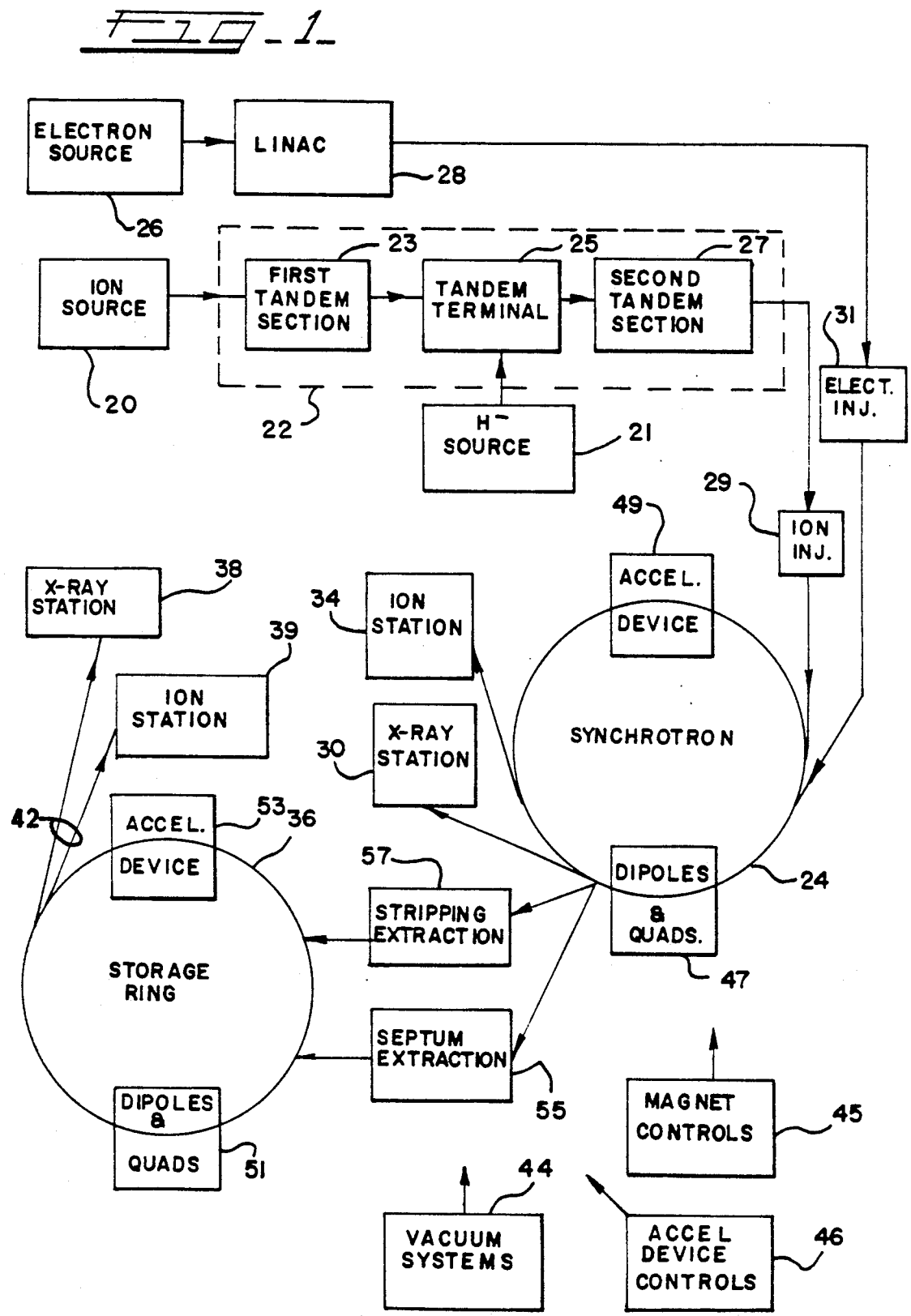
FIG. 1 is a block diagram of some of the principal components of the present invention.

FIG. 1 is a block diagram of the principal components of the present invention. In FIG. 1, an ion source 20 produces negative ions that are taken to a tandem accelerator 22, comprising a first tandem section 23, a tandem terminal 25, and a second tandem section 27. If the accelerator is to be used for ion radiography or ion therapy, the ion source and tandem may be used to produce either protons (H+) or other positive ions. Negative hydrogen ions (H−) are produced in an H− source 21 which would be located in the tandem terminal 25. Alternatively, if negative ions are to be utilized, they could be produced by a source in the terminal of a single-ended preaccelerator or the like. Other possible ions of interest include D− (negative deuterium), D+ (positive deuterium), T− (negative tritium), T+ (positive tritium), alpha particles He++ (helium ion), Li+++ (lithium ion), Li− and carbon ions of various ionization states ($C^{+n}$). The selected ions are produced in a duoplasmatron or the like, are accelerated appropriately and are injected by an ion injector 29 into a synchrotron 24 to be accelerated further. They could also be utilized in a separate work station.

An electron source 26 is used when it is desired either to have a beam of accelerated electrons for radiation therapy or any other purpose or when the objective is to use the synchrotron radiation from an accelerated beam of electrons to produce X-rays. The electrons are taken to a linear accelerator (linac) 28 where they are accelerated for injection by an electron injector 31 into the synchrotron 24, or utilized in a separate work station for radiation therapy.

The electron injector 31 may be, but is not required to be, the same apparatus as the ion injector, recognizing that the magnetic rigidity of 50 MeV electrons is nearly the same as that of 1.5 MeV H− ions. The magnetic rigidity is defined as the product of the strength B of the magnetic field bending a beam and the radius r of curvature of the bend. Particles accelerated to appropriate energy levels may be used directly from the synchrotron 24. Thus, if electrons from the electron source 26 are the input particles, they may be used to provide X-rays at an X-ray station 30 from the synchrotron 24.

If the ion source 20 originates the particles that are accelerated, then the synchrotron may be used to produce a beam of accelerated ions at an ion station 34. When these ions are positive ions, septum extraction from the synchrotron will be required, while the simpler stripping extraction may be utilized when the ions are negative ions from source 21. Septum extraction of negative ions may also be provided when it is desired to utilize the negative ions directly in the work station. In the alternative, accelerated particles of any type may be switched to a storage ring 36 where the electrons may be used to produce X-rays from synchrotron radiation at any of a large number of X-ray stations 38. Ions may be extracted to an ion station 39. The equipment of FIG. 1 is served by vacuum systems 44, magnet control system 45, and accelerating device controls 46. These control dipole and quadruple magnets 47 and accelerating devices 49 in the synchrotron 24, and also dipole and quadruple magnets 51 and accelerating devices 53 in the storage ring 36.

While the equipment shown symbolically in FIG. 1 could be used in many ways, the advantages of the invention are achieved most effectively if electrons are supplied from a source 26 and accelerated in the linear accelerator 28 and the synchrotron 24. They can be switched at the end of each acceleration cycle to load the storage ring 36 over several pulses of a total duration of at most a few minutes. It is expected that the storage ring 36 will be used to circulate electrons at a controlled energy level to produce X-rays of a predetermined range of wavelengths. Use of the storage ring 36 to produce beams of electrons or ions 42 will be more infrequent than use of the storage ring to produce the X-rays from synchrotron radiation to the work station 38.

After the storage ring 36 is filled with electrons, it is a relatively simple matter to switch to the use of the ion source 20 to produce ions that are accelerated in the tandem accelerator 22 and the synchrotron 24 to produce beams of ions 42 for therapy or radiography. This can be done while the storage ring is continuing to produce X-rays for periods as long as six to ten hours. The accelerating device 53 adds energy to make up for that lost due to synchrotron radiation, keeping the beam energy constant. The apparatus shown symbolically in FIG. 1 is thus readily adapted for use both as a medical apparatus for ion therapy or ion radiography and also as an apparatus for producing X-rays for photolithography. The range of energies that are appropriate for medical use of ions is well, met by a synchrotron that is also capable of accelerating electrons to an energy that produces X-rays of an appropriate wavelength. This will be treated more specifically below.

FIG. 2 is a schematic view of one arrangement of equipment for the practice of the present invention. In FIG. 2, a synchrotron 50 accelerates particles that are switched by a tube 52 to a storage ring 54. A wall 56 separates a medical area 58 from a semiconducting processing area 60. The tube 52 may be tens of feet in length, to provide substantial separation between the synchrotron 50 and the storage ring 54.

An alternate arrangement of equipment for the practice of the present invention is shown in FIG. 3. In FIG. 3, a synchrotron 64 is connected by a tube 66 to a storage ring 68 that is substantially concentric with the synchrotron 64. When the storage ring 68 is circulating electrons, X-rays would be utilized in the semiconducting processing region 74 while ions from the synchrotron 64 would be transported by a transport line 71 to a medical region 72 quite removed from semiconducting processing region 74.

Electron synchrotron radiation is being used in many installations for research purposes including development of X-ray lithography, as described above. X-rays in a wavelength range of 6 to 10 Angstroms represent a preferred range in the future for producing an acceptable resolution in imaging semiconductor masks to produce integrated circuits with spacings of one quarter micron or less. These research facilities contain acceleration systems in the storage ring to maintain the beam circulation by replacing the energy which is lost, primarily as the radiation of X-rays. After the storage ring is loaded, the synchrotron has no further function in producing X-rays until the process needs repeating, and it can be switched over to produce ions for purposes such as medical therapy, imaging or non-destructive testing. None of the existing research installations use the accelerator systems in this manner.

FIG. 4 is a sectional view of a portion of the synchrotron 24 of FIG. 1 and also of the storage ring 36 of FIG. 1. In FIG. 4, a beam 80 of electrons or ions is shown in cross-section in a beam tube 82. A dipole magnet 84 includes a coil 86 and a ferromagnetic core 88. A vacuum is maintained inside the beam tube 82 by a standard primary vacuum system which is not shown by and also by a getter plate 90, which acts as a distributed pump of very high pumping speed. The getter plate 90 is made of an alloy of zirconium and aluminum or other substance that adsorbs molecules readily and emits the adsorbed molecules when heated during an outgassing process. Operation of the synchrotron 24 or storage ring 36 of which the apparatus in FIG. 4 is a part is enhanced by applying a dc voltage of the order of tens or hundreds of volts between the getter plate 90 and the conducting wall of the vacuum chamber. This produces an electric field that attracts positive ions to the getter plate 90, where the ions are adsorbed and removed as loose particles from the interior of the beam tube 82. This prevents defocusing of the electron beam 80 by positive ions produced by interaction of the electrons with residual gas in the chamber. The positive ions are otherwise attracted to the beam 80 and held in the beam by a potential well.

FIG. 5 is a view of one possible arrangement of the small straight magnets of the synchrotron of the present invention. In FIG. 5, a ring 93 comprises eight octants 94, each comprising eight dipole bending magnets 95 and two quadrupole focusing magnets 96. The complete synchrotron thus comprises 64 dipole bending magnets and 16 quadrupole focusing magnets. Each octant has a kicker magnet 97, the function of which will be described below. The ring 93 has one or more rf accelerating cavities 98. A foil station 99 in each octant is used for stripping extraction, which may be to a beam dump 100 or to a point of use 101. The ring 93 is shown as substantially circular, but it should be evident that the straight sections between dipole magnets 95 can be extended if desired. An injector 29 and 31 injects either electrons or ions that are put into a proper orbit by a kicker magnet 102 and a second kicker magnet 103. The magnet configuration of FIG. 5 applies equally to the storage ring 36 of FIG. 1.

A small synchrotron with many short straight dipole magnets has a significant advantage over one with the conventional curved magnets. It is easy to manufacture magnets at lower cost. In addition, straight magnets significantly increase the flexibility of the synchrotron and storage ring by allowing any combination of diameter (and hence energy) and focusing arrangement of magnets and straight sections. This allows the designer to change the length of a straight section and the number of straight sections to permit other types of extractions of ions and the insertion of devices such as wigglers, undulators, and free-electron lasers for electron machines. It also allows rearrangement of focusing quadrupole magnets to allow shifting to the "high brightness" arrangement. The latter is a circulating beam of very small diameter, which is characteristic of those used at physics facilities. The short straight magnets also are of a suitable length and aperture to allow charge-exchange extraction at many points around the ring by passing the negative ion through a thin foil upstream of a single dipole magnet to strip the ion and allow its extraction for detection. The use of multiple extraction points with window-frame foils disposed around the ring allows for simple tuneup and precision alignment of the synchrotron. This requires ions that can be simply extracted by passing through foils. This includes ions such as $H^-$, $D^-$, $T^-$ ions, $H_2^+$, $He^+$, and molecular ions. It results in simpler tuneup and alignment than normal procedures, which are to use sophisticated non-destructive diagnostics at many points within the ring vacuum chamber. The use of multiple extraction points to detect the beam edges in tuneup does not require non-destructive diagnostics within the ring vacuum chamber. The procedure is useful for synchrotrons and storage rings intended to accelerate and store such ions, as well as machines for electrons or any other ion. The latter would require an additional injector for the negative ion which would not otherwise be required.

Another advantage of multiple stripping extraction is that it provides a synchrotron or storage ring with low residual radioactivity when used with the ions which can be extracted with the foils. Foil extraction efficiency is very high, of the order of 99%. Any mistuning, component failure, or accident would result in beam movement across the vacuum chamber aperture that is slow compared to the revolution time of the beam (tenths of microseconds) so that the beam would strike one of the windowframe foils (inside, outside, top, or bottom), placed at all points of maximum oscillation amplitude, before striking the sides of the vacuum chamber. After passing through the foil, the ions would have different charge states and would be extracted from the synchrotron after passing through the next bending magnet. Such ions could be collected in a local external beam dump which is well shielded and could be removed if it becomes too radioactive. Residual activity of the machine itself, therefore, is unusually low. This feature is particularly significant for the acceleration of $D^-$ ions since neutrons, which are prolific in causing radioactivity in materials, are produced with very low energy deuterons. The neutron-proton binding energy in the deuteron is only 2.3 MeV.

Use of getter strips is known to be good for very high base vacuum and makes it possible to achieve a vacuum of the order of $10^{-10}$ Torr. Such high vacuum is important for electron storage rings and acceleration of negative ions. Biasing the getter strip with an electric voltage also makes it operate as a nearly full-circle clearing field to remove positive ions produced by collision of the electron beam with residual gas atoms. The positive ions can be trapped and can destroy (by overfocusing) the circulating electron beams.

FIG. 6 is a view of a portion of an accelerator showing a means of injecting electrons and ions. In FIG. 6, an ion preaccelerator 110 is a duoplasmatron or the like producing a beam of $H^-$ particles at about 1.5 MeV while the electron linac 112 produces electrons at energies of the order of 50 MeV. These charged particles have nearly the same magnetic rigidity and therefore can be injected through the same magnetic injection system. In the alternative, separate injection systems could be used. Injection is accomplished by energizing a dipole magnet 114 to bend the charged particle beam onto the proper orbit of the ring magnet system. The charged particles enter the straight section 116 and are bent by the dipoles 118 to circulate around the ring. When the beginning of the beam again passes through the injection dipole magnet 114, the magnet 114 is deenergized so that it has no effect on the beam that is circulating. For this particularly simple injection technique, the injected pulse duration must be less than the revolution period of the charged portion around the ring by the time required to reduce the field of the injection dipole 114 from its full value to zero. The injection dipole 114 must thus be a magnet that can be de-energized rapidly such as a ferrite magnet, which can be deenergized in 50 nanoseconds. For the size of the present ring (equivalent to a radius of 22.5 feet), the period of revolution is approximately 2 microseconds for 1.5 MeV H-ions, and 140 nanoseconds for the faster 50 MeV electrons travelling essentially at the speed of light. The injected pulse duration can thus be more than half a revolution period for either ions or electrons. More sophisticated injection techniques allowing multiturn injection are also possible, but are not needed in the present application.

To inject 50 MeV electrons, the magnet 120 is energized to deflect electrons onto the injection line. The magnet 120 can be an iron electromagnet operated in the DC mode or in a slow pulsed mode. To inject $H^-$ ions or other ions from the source and preaccelerator 110, a similar magnet 122 is energized while the magnet 120 is de-energized. An alternative ion injector 122, for instance, for ions of $H^+$, $D^-$, $He^{2+}$, $C6+$, and the like, could be placed along the injection beam line to inject ions into the ring by de-energizing both the magnets 120 and 124. Means can also be provided to use beams from any of the injectors for other applications when they are not being used to inject particles into the ring. The shift from injecting one type of particle to another can be accomplished in the time it takes to energize and de-energize the magnets 120 and 122, and this can easily be accomplished in seconds.

Quadrupole magnets (not shown) would be included in these beam lines to match the optical properties (beam sizes and divergences) to those required in the rings. A diagnostics station 126 is shown in the figure in order to monitor the correct matching of the beam to be injected when the dipole 114 is not energized.

Different modes of extraction are provided for the different applications. For electrons, the requirement is to extract the circulating beam as a whole at full energy in one revolution of the synchrotron. This is called fast extraction. The extracted beam is injected into the storage ring. This fast extraction requires a single fast bump magnet in the ring and a thin septum magnet to remove the charged particles from the ring. The bump magnet shifts the orbit enough to direct the beam into the septum magnet, which deflects the beam to extract it.

FIG. 7 is a schematic view of an electron extraction system. In FIG. 7, a beam tube 130 represents a straight portion of the circulating tube of the accelerator. The circulating beam occupies less than half the circumference of the ring because of the phase stability of the radio-frequency accelerating system. During the time when there is no beam at the position of a fast bump magnet 132, the bump magnet 132 is energized in a time of the order of 50 nanoseconds. When the beam then passes through the bump magnet 132, the beam is given an angular deflection. The angular deflection translates to a radial displacement of the beam. The displacement is a maximum at one-fourth of an oscillation wavelength downstream and is adequate to move the beam across the thin septum of a septum magnet 134 which then deflects the beam into an exit tube 136. When the beam is not bumped, it continues to circulate in a beam tube 138. Injection of this high-energy beam from the synchrotron into a storage ring can be just the inverse of this extraction process although some modification is required to inject many synchrotron pulses into the storage ring. The electrons first pass through a septum magnet 140 which places them in the ring in an orbit slightly displaced from the desired circulating orbit but parallel to it. The displaced beam crosses the desired circulating orbit a quarter of an oscillation wavelength downstream, at which point a fast bump magnet 142 deflects the beam onto the proper circulating orbit. The fast bump magnet 142 must then be de-energized before the injected beam reaches this point on the next turn around the ring. This fast transfer can take place in either the vertical or horizontal direction. Extraction and fast injection in the vertical direction would allow the synchrotron and storage ring to be one above the other so that the total transfer could take place in one straight section. The possibility of extraction from the storage ring would also be provided when one wanted to dump the beam circulating in the storage ring. This might be desired when the circulating current has gotten low enough that one wants to refill the ring, when one wants to shut the ring down, or when a fault is detected which would cause beam loss in an arbitrary manner or position.

For transferring multiple synchrotron pulses into the storage ring, only necessary when the storage ring is to be refilled with electrons, an orbit bump in the storage ring is created by two or more bump magnets to place the damped circulating beam close to the thin septum, a new turn is injected with small betatron oscillations, and the orbit bump is removed quickly (in a few turns) to move the beam away from the septum. The oscillations of the newly injected pulse damp in a few milliseconds to make it merge with the main circulating beam before the next pulse is added. The process can be repeated as many times as needed until the desired total current is accumulated.

The same fast extraction and injection system also works with ions. The latter would be used for proton therapy if the storage ring were used as a stretcher ring for therapy with H⁻ions or other ions in order to get 100% beam use duty cycle (with slow stripping extraction of protons or other ions from the storage ring) at the same time as high current by cycling the synchrotron rapidly. The magnetic rigidity of 250 MeV H.ions is only one half that of 1.5 GeV electrons, but the cross-section of the circulating ion beam would be larger than that of the circulating beam of electrons. The ion beam sizes do not damp the way electrons do because of synchrotron radiation. Thus, a larger deflection angle is required in order that the beam completely cross the septum. Therefore, the same fields in the fast bump magnet will suffice for either electrons or negative hydrogen ions.

FIG. 8 is a system for slow extraction of protons by charge exchange of H.ions in stripping foils. One fast kicker magnet 150 is placed one octant, approximately a quarter oscillation wavelength, ahead of the stripping foil 152, and a second fast kicker magnet 154 is placed about a quarter wavelength downstream. The kicker magnets 150 and 154 are energized to displace or bump the orbit at the foil 152 by a very small amount and to remove this orbit bump one octant later. The small amount of beam penetrating the foil will lose its two electrons, change from a negative ion to a positive ion, bend in the opposite direction in the following dipole 156 magnet just before a straight section, and exit the machine. The amount of beam that strikes the foil is controlled by feedback from a current monitor in the extracted beam to the two kicker magnets. FIG. 9 is a cross-sectional view of the foil 152 inside the vacuum chamber 162. The foil 152 is in the form of a window frame that is open to pass the beam 160. The foil 152 is typically an aluminum or carbon foil having a density of less than 1 milligram per square centimeter. The beam can be displaced vertically, to hit the top or bottom of the foil, or horizontally, to hit the foil inside or outside. In any of these cases, a beam that hits the foil will change from negative to positive and will exit outward from the ring in passing through the next dipole magnet.

An accelerator of negative ions can have unusually low residual radioactivity. This is particularly important for negative deuterium ions because of their propensity for producing neutrons at low energies, at and above 2 MeV. If these window-frame stripping foils such as the foil 152 are placed one magnet upstream of each straight section, then any beam that would otherwise be lost in the machine, due to steering errors, rf frequency tracking errors, magnet faults, and the like, all slow compared to the time it takes beam to travel one octant, will strike one of the foils before it hits the side of the vacuum chamber wall and will be extracted into a local beam dump. The only exceptions are those negative ions that were neutralized by collisions with the residual gas in the vacuum. These are expected to be less than one percent of the circulating beam in a vacuum of $10^{-10}$ Torr. In a C magnet with an opening to the outside of the ring, even these neutral atoms will pass in a straight line through the aluminum vacuum chamber, producing low residual activity, and they will not interact in the magnet iron where the residual activity would have a much longer half life.

FIG. 10 is a sectional side view of a beam dump. A beam tube 170 receives beam deflected out of the accelerator or storage ring by a bending dipole. A steel block 172 is backed by a concrete cap 174, and the steel block 172 and concrete cap 174 are enclosed in a concrete shield 176. The steel block 172 is typically four inches in diameter and 18 inches in length, and the concrete cap 174 is the same diameter and a foot in length. The concrete shield 176 is substantially cylindrical, about two feet in diameter and four feet long. One beam dump in the accelerator has to be quite well shielded because it would serve to accumulate residual beam perhaps as much as 5-10%, that is extracted deliberately on each pulse. There must be enough beam each pulse to complete a therapy scan, so some will be left over at the end of a scan. This must be disposed of before the magnet is recycled for the next pulse.

FIG. 11 is a sectional view of the beam tube showing a zirconium-aluminum getter strip 180. The getter strip 180 is insulated from the vacuum chamber walls 182 by a standoff 184, and extends longitudinally all along the vacuum chamber walls 182 and so essentially around the entire circumference. A current is passed through the getter strip 180 to reactivate it when it becomes saturated with gas. If a voltage is applied between the getter strip 180 and the wall 182, an electric field will exist between the strip 180 and the vacuum chamber wall 182. The electric field will remove ions from the interior of the vacuum chamber.

The basic pressure for accelerating negative hydrogen ions in the accelerator is of the order of $10^{-10}$ Torr. This level of vacuum is accomplished by non-evaporable zirconium-aluminum getter strips, backed by small ion pumps to pump methane and noble gases that are not pumped by the getter strips. The residual gases are typically 95% hydrogen and 5% oxygen. With this composition, less than 0.5% of the circulating negative hydrogen ions are lost due to collisions with residual gas atoms in an acceleration time of 0.3 sec. The cross-sections for this interaction are greatest at low ion energy, and the loss would be an order of magnitude greater at the same pressure if the residual gas were predominantly oxygen or nitrogen, as it would be if there were small vacuum leaks. Even with the weak on beams projected for cancer therapy, $2 \times 10^{10}$ ions/pulse and 0.5% loss due to gas interactions (predominantly neutralization of the H-ion), approximately $10^8$ ions will be lost in 0.3 sec. The resulting neutral hydrogen atoms are not affected by the magnetic field and hence hit the outer wall of the vacuum chamber in the direction they were travelling at the time they were neutralized (tangent to the circulating orbit except for a very small correction due to transverse oscillations). The neutral atom is stripped to an electron and a proton in the wall of the vacuum chamber. For proton energies above about 20 MeV, the proton is energetic enough to penetrate the thin wall of the vacuum chamber and can be detected on the outside of the chamber.

FIG. 12 is a sectional end view of the accelerator showing an apparatus for measuring ions which exit the ring as neutrals after interacting with the residual gas, and FIG. 13 is a sectional top view taken along section lines 12—12 of FIG. 12. In FIGS. 12 and 13, a beam tube 190 encloses a beam 192 of negative hydrogen ions that are being accelerated or stored. A C-magnet 194 is energized by coils 196 and 198 to provide an appropriate bend to the negative hydrogen ions to circulate them around the ring. When a negative hydrogen ion interacts with a residual gas atom, the most likely result is that the loosely bound electron will be removed from the ion, resulting in a neutral hydrogen atom. The atom continues in the direction it was traveling before the interaction and exits the machine, unaffected by magnetic fields, through the open side of the C-magnet. It will penetrate the outer wall of the vacuum chamber as a proton and strike a detector 200 that is disposed outside the beam tube 190. The detector 200 is typically a coaxial ion chamber in which the center conductor 202 is held at a high voltage, typically several hundred volts, or more, and the sheath 204 is at ground. A gas 206 is between them. The detector 200 may be continuous around the ring, or alternatively, there may be individual chambers throughout each octant. The circumferential position of the discharge induced by the proton, and hence of a leak, could be determined by timing differences between the signal from each end of the coax. The circumferential position of the collision between an ion and a gas atom can be determined by projecting back from the discharge position in the coax by a tangent to the circulating beam orbit. This represents a continuously operating leak detector and locator.

The counting rate at any circumferential position is directly proportional to the beam intensity and the residual gas pressure at a corresponding point in the ring, and is related to the ion energy. Since the beam intensity and the ion energy at any time during the cycle are known, the measurement gives the local gas pressure very sensitively everywhere around the ring. It thus can detect trouble spots, areas giving unusual outgassing, or very tiny leaks around the ring. The latter are very important for very high vacuum systems. FIG. 12 shows a C-magnet 194, but the system would work equally as well with an H-magnet with the coax inside the iron yoke but outside the vacuum chamber, or any other form.

In the alternative, the detector 200 could be a portable system using a scintillator and photo-multiplier tube that could be positioned at any point around the ring on the outside. While such a system would measure a signal at only one point per detector at one time, successive measurements at different positions could survey the pressure around the ring.

Such a detector might also be constructed primarily to measure neutrons. Many types of counters currently in use might be used for this purpose. Depending on energy, protons entering the outside iron yoke of H-magnets would produce neutrons. The protons would not penetrate the total iron thickness, but the neutrons produced could be detected outside the H-magnet. For C magnets, where there is no iron in the path of the protons, a detector could be made sensitive only to neutrons by including in the detector an absorber thick enough to stop the protons, and in which the protons would produce neutrons by spallation that would penetrate the absorber and enter the detector. An advantage of measuring neutrons only might be to give lower background than otherwise.

The ease of charge-exchange (stripping) extraction of H-ions at many points around a ring makes possible a simple and inexpensive method of precision alignment and tuneup of any ring, whether designed for H.ion acceleration or not.

Alignment with survey equipment and present techniques is very important to get reasonably close to the desired result, adequate to allow the beam to be circulated around the ring so that beam measurements can be made. The final alignment to the precision required, however, has to be made using measurements on the circulating beam. This is because alignment errors are magnified by the quadrupoles, and many kinds of magnet errors contribute to the problems of alignment. A common procedure is to have many detectors within the ring which measure the horizontal and vertical beam distributions and beam centroid position at each detector as a function of time over many revolutions. One can then determine the position about which the beam is oscillating. The goal is to adjust correction magnets, move quadrupoles, or other correction methods, to make the beam centroids coincide with the centers of the magnets and vacuum chambers. This allows a maximum space to contain beam oscillations within the vacuum chamber. Many detectors are required, a minimum of one horizontal and one vertical detector per quarter oscillation wavelength. These must be nondestructive; that is, they must operate on induction principles and not interfere with the circulating beam. Such detectors are normally quite sophisticated.

The same result can be achieved with H⁻ beams by displacing the circulating beam at the window frame foil 152 of FIG. 8 by a known amount and measuring the number of ions that pass through the foil and are extracted as protons. This number as a function of the displacement determines the beam distribution at the position of the foil. The displacements can be vertically up or down or horizontally toward the inside or outside. The displacement is created by the fast kicker magnet 150 of FIG. 8 in the straight section before the stripper foil 152, and is removed by the kicker magnet 154 in the straight section after the extraction straight section. For alignment, the kicker magnets 150 and 154 need to be rotatable so that their fields can be either horizontal or vertical. Since the circulating beam occupies only half of the circumference of the ring, the individual revolutions are separate and one can energize the kicker magnets 150 and 154 to measure the parameters at any turn. If beam on the succeeding turn interfered with the measurement, the remaining beam could be completely extracted into the beam dump before it came around to the extraction point a second time, or else a time gate at the detector could reject extracted beam from the succeeding turn if such interference occurred.

Such measurements of extracted beam as a function of displacements can be made every quarter oscillation wavelength around the ring. This would be at eight points around the accelerator. Since both horizontal and vertical measurements can be made at each point, this is equivalent to the normal practice of tuneup. In this case, however, the detectors do not have to be contained within the ring, occupying valuable straight-section space, and do not have to be non-destructive. Therefore, they are simpler and considerably less expensive. The result might also be simpler to analyze.

A procedure simpler than measuring extracted current versus displacements to measure distributions is to find the displacements that only detect the edges of the circulating beam, inside and outside, top and bottom. This gives, beam size and centroid (by sum and difference of displacements compared to window size) and would be adequate if the beam distribution were symmetrical, which is likely.

The beam detectors need only be simple scintillation counters to measure the number of protons extracted, although a split counter to distinguish between beam extracted by hitting the outside or the inside of the foil could be useful to serve also as a diagnostic of RF tracking errors and other possible problems.

FIG. 14 is a spectrum of photon flux as a function of wavelength for typical synchrotron radiation. This spectrum is characterized by a critical wavelength which is preferably in the range of 6–10 Angstroms for X-ray lithography. X-rays of longer wavelengths can be filtered to prevent their incidence on a sample for lithography, and the spectrum is cut off rapidly at shorter wavelengths. The critical wavelength can be adjusted by changing electron energy in the storage ring.

The description of specific embodiments of the present invention is intended to set forth the best mode known to the inventor for the practice of the invention. It should be taken as illustrative and not as limiting, and the scope of the invention should be limited only by the appended claims.

What is claimed is:

1. An apparatus for producing X-rays by electron synchrotron radiation and also beams of accelerated ions comprising: a) a source of ions; b) a source of electrons; c) an electron preaccelerator receiving and preaccelerating the electrons; d) an ion preaccelerator receiving and accelerating the ions; e) a synchrotron connected to the preaccelerators for accelerating electrons and ions to produce accelerated electrons and accelerated ions; f) a storage ring connected to the synchrotron to store accelerated electrons and ions; and g) a plurality of work stations utilizing beams of accelerated ions and X-rays.

2. The apparatus of claim 1 in which accelerated electrons stored in the storage ring at a predetermined energy level produce X-rays at a work station by synchrotron radiation of the electrons where the accelerated stored electrons are deflected by magnets within the storage ring, and in which work stations for charged particles of an energy level that may be different from the predetermined energy level of the accelerated stored electrons are connected to the system including the synchrotron and the preaccelerators.

3. The apparatus of claim 2 wherein the charged particles are electrons.

4. The apparatus of claim 2 wherein the charged particles are ions.

5. The apparatus of claim 2 in which the work station connected to the storage ring is a work station for X-ray lithography.

6. The apparatus of claim 2 in which the work station connected to the storage ring is a medical station using synchrotron radiation.

7. The apparatus of claim 2 in which the source of ions comprises a source of particles selected from the group consisting of protons, negative hydrogen ions, and heavier ions that are accelerated in the synchrotron, and wherein a work station is connected to the synchrotron to utilize these ions.

8. The apparatus of claim 7 in which negative hydrogen ions are accelerated in the synchrotron with stripping extraction for applications of protons and deuterons.

9. The apparatus of claim 7 in which negative deuterons are accelerated in the synchrotron with stripping extraction for applications of protons and deuterons.

10. The apparatus of claim 2 wherein one of the work stations that are connected to the electron preaccelerator comprises an electron work station that receives a beam of accelerated electrons for radiation therapy of cancer and for non-medical applications of high-energy electrons.

11. The apparatus of claim 2 wherein one of the work stations is connected to the ion preaccelerator to form a low-energy ion work station for proton-induced X-ray emission.

* * * * *